United States Patent
Reidmeyer et al.

(10) Patent No.: US 6,315,880 B1
(45) Date of Patent: *Nov. 13, 2001

(54) CHEMICAL PLATING METHOD, ELECTROLYTIC CELL AND AUTOMOTIVE OXYGEN SENSOR USING IT

(76) Inventors: Mary R. Reidmeyer, Rte. 1, Box 230-A, Freeburg, MO (US) 65035; Matthew J. Donelon, 309 Hawbrook Pl., Jerseyville, IL (US) 62052; Robert F. Killion, 14614 Old Halls Ferry, St. Louis, MO (US) 63034

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/953,864

(22) Filed: Oct. 16, 1997

(51) Int. Cl.[7] .............................. G01N 27/407; B05D 5/12
(52) U.S. Cl. ...................... 204/424; 204/421; 427/105; 427/125; 427/264; 427/265; 427/376.7; 427/404; 427/419.1; 427/443.2
(58) Field of Search ..................................... 204/421–429; 427/105, 125, 243, 264, 265, 270, 376.7, 404, 419.1, 443.2, 229, 299, 383.5, 443.1

(56) References Cited

U.S. PATENT DOCUMENTS

| | | | |
|---|---|---|---|
| 3,400,054 | * 9/1968 | Ruka et al. ........................ | 204/427 |
| 3,562,911 | 2/1971 | Walter et al. . | |
| 3,844,920 | 10/1974 | Burgett et al. . | |
| 3,978,006 | * 8/1976 | Topp et al. ......................... | 204/429 |
| 4,136,000 | 1/1979 | Davis et al. . | |
| 4,152,234 | * 5/1979 | Pollner ............................... | 204/427 |
| 4,169,777 | 10/1979 | Young et al. . | |
| 4,186,071 | 1/1980 | Romine et al. . | |
| 4,199,425 | * 4/1980 | Sinkevitch ......................... | 204/429 |
| 4,225,634 | * 9/1980 | Tanaka et al. ..................... | 427/125 |
| 4,253,934 | 3/1981 | Berg et al. . | |
| 4,265,724 | * 5/1981 | Haecker et al. .................... | 204/429 |

(List continued on next page.)

FOREIGN PATENT DOCUMENTS 4-95766 * 3/1992 (JP) .

OTHER PUBLICATIONS

Hackk's Chemical Dictionary, 4th ed., (1969) Month unavailable, p. 7.*
Vassell, et al., "Extended Range Air–To–Fuel Ratio Sensor", Passenger Car Meeting Dearborn, Michigan, Oct. 1–4, 1984.
Hetrick, et al., "Oxygen Sensing by Electrochemical Pumping", International Congress and Exposition, Cobo Hall, Detroit, Michigan, Feb. 23–27, 1981.

*Primary Examiner*—T. Tung
(74) *Attorney, Agent, or Firm*—Polster, Lieder, Woodruff & Lucchesi

(57) ABSTRACT

An automotive lambda oxygen sensor is formed by electroless plating of a thin, catalytically active, conductive electrode uniformly on the outer surface of a zirconia thimble. The process includes forming a pristine zirconia solid electrolyte thimble and drilling out a cylindrical cavity in it. A porous outer surface suitable for producing crystallization sites is formed by dipping the unfired thimble in a zirconia slurry containing spray-dried microspheres and firing the coated thimble to densify the thimble and the microspheres and to produce cavities on the surface of the thimble. An inner platinum electrode is formed by conventional conductive ink painting on the axial cavity of the sensor, and the sensor is again fired. The surface is activated by immersion in an acetone chloroplatinic acid bath to form multiple crystallization points, heat treated, then plated in an electroless platinum bath to a desired thickness. After plating, the sensor is heat treated and a conventional spinel glaze coat is flame sprayed over the sensor. The process produces sensors which consistently provide rapid response times and stable operation.

10 Claims, 2 Drawing Sheets

U.S. PATENT DOCUMENTS

| | | |
|---|---|---|
| 4,294,668 | 10/1981 | Young . |
| 4,418,099 * | 11/1983 | Cuevas et al. ............... 427/229 |
| 4,477,487 | 10/1984 | Kojima et al. . |
| 4,741,816 * | 5/1988 | Nishio et al. ............... 204/425 |
| 4,824,550 | 4/1989 | Ker et al. . |
| 4,830,880 * | 5/1989 | Okubi et al. ............... 427/229 |
| 4,897,174 | 1/1990 | Wang et al. . |
| 5,049,255 | 9/1991 | Wolfe et al. . |
| 5,281,635 * | 1/1994 | Bishop ............... 427/229 |
| 5,288,389 | 2/1994 | Yamada et al. . |
| 5,443,711 | 8/1995 | Kojima et al. . |
| 5,472,591 * | 12/1995 | Saito et al. ............... 204/429 |
| 5,480,535 | 1/1996 | Kondo et al. . |
| 5,520,789 | 5/1996 | Takahashi et al. . |
| 5,716,507 * | 2/1998 | Tanaka et al. ............... 427/125 |
| 5,948,225 | 9/1999 | Katafuchi et al. . |
| 5,989,624 | 11/1999 | Kida et al. . |

\* cited by examiner

CHEMICAL PLATING METHOD, ELECTROLYTIC CELL AND AUTOMOTIVE OXYGEN SENSOR USING IT

BACKGROUND OF THE INVENTION

This invention relates to solid state electrolytic cells and to oxygen sensors utilizing them. It has particular utility as a highly stable, rapid response lambda oxygen sensor in an automotive exhaust system.

Solid state electrolytic cells are well known. A particularly useful cell includes a solid electrolyte which selectively transmits oxygen and which includes catalytic electrodes on opposed sides of the solid electrolyte. Such cells are widely used as automotive lambda (stoichiometric) exhaust gas sensors, where they produce a voltage signal which is highly dependent on the amount of oxygen in the exhaust gas stream. It will be understood, however, that the usefulness of the invention is not limited to such sensors. For example, multiple such cells can be connected as non-stoichiometric, pumping oxygen sensors. See, for example, Kondo et al., U.S. Pat. No. 5,480,535. In other uses, when connected as a current generator, such cells act as fuel cells, and when an external voltage is applied, they can act as oxygen generators which produce exceptionally pure oxygen.

A common configuration of an automotive lambda exhaust gas sensor is a small thimble-shaped body of compacted zirconia (zirconium dioxide) stabilized with about 2–10 mole percent yttria ($Y_2O_3$) and, optionally, 0–20 mole percent alumina ($Al_2O_3$). The catalytic electrodes can be painted on as a platinum ink. Commonly, the outer electrode is formed by vacuum sputtering a thin film onto substantially the entire outer surface of the thimble. The sputtering process is expensive and inefficient, the electrodes are of varying thickness from one axial end of the thimble to the other, and the resulting sensors are unpredictable and have high reject rates.

The basic operation and known problems of an automotive lambda exhaust gas sensor are described, for example, in Topp et al., U.S. Pat. No. 3,978,006, Burgett et al., U.S. Pat. No. 3,844,920, Romine et al., U.S. Pat. No. 4,186,071, and Berg et al., U.S. Pat. No. 4,253,934. As set out in these patents, it is desirable for the sensor to have switching times on the order of under 200 milliseconds when the air-to-fuel ratio fed to the engine switches from lean to rich or rich to lean with respect to the stoichiometric ratio. It is also desirable for the sensor to produce smooth switches of at least about 200 to 300 millivolts when the air-fuel ratio switches. In recent years, the time required for an oxygen sensor to reach its operating temperature has also been recognized as a significant problem, and heated oxygen sensors have become standard. It is thus also desirable to produce an oxygen sensor which is well suited to introduction of a heater into the sensor structure. The background of heated oxygen sensors is well set out, for example, in Ker et al., U.S. Pat. No. 4,824,550.

SUMMARY OF THE INVENTION

One object of the present invention is to provide a solid-state electrolytic cell which is simple and inexpensive to manufacture.

Another object is to provide such a cell which, when utilized as a lambda oxygen sensor produces rapid response times and high signal strength.

Another object is to provide such a cell which is reliable and reproducible.

Another object is to provide such a cell which is easily adaptable to use with a heater.

Another object is to provide a simple, reliable, high-performance oxygen sensor which incorporates such a cell.

These and other objects will become apparent to those skilled in the art in light of the following disclosure and accompanying drawings.

In accordance with one aspect of the invention, generally stated, a solid electrolyte cell is provided comprising a solid electrolyte body having a first side and a second side, a first electrode on the first side of the body, the first side of the body having a porous surface comprising a plurality of substantially spherical recesses, a first electrode substantially covering the first side of the body, the first electrode comprising a thin layer of conductive catalytic material extending into the recesses to mechanically lock the layer to the first surface, and a second electrode on the second surface of the body. The cell is preferably an oxygen sensor installed in the exhaust system of a combustion system, most preferably of an internal combustion engine. In a preferred embodiment, the cell is a lambda oxygen sensor formed as a thimble, the first surface being the outside of the thimble. The layer is plated on the first surface and is of substantially uniform thickness from a closed axial end of the thimble to near an open axial end of the thimble.

Preferably the solid electrolyte is a yttria-stabilized zirconia, having an yttria content of about two to ten percent yttria, most preferably having a mole percentage of yttrium of about 3–6% and a mole percentage of alumina of zero to twenty percent. The electrodes are preferably formed of platinum, rhodium, or palladium, most preferably platinum.

In accordance with another aspect of the invention, a method is provided of forming a solid electrolyte cell, the method comprising a step of forming a solid electrolyte body including a porous layer on a first surface of the body, a step of activating the first surface of the porous layer to form a plurality of growth points for a conductive layer on the first surface, a step of forming a first electrode by plating a conductive layer on the activated first surface of the body, and a step of forming a second electrode on a second surface of the body. Preferably, the porous layer comprises substantially spherical recesses which are formed by coating the body with a slurry of solid electrolyte including in the slurry spray-dried balls of the electrolyte. On firing the body, the spray-dried balls are densified to form small balls of solid electrolyte at the bottoms of substantially spherical recesses. The plating process preferably includes activating the first surface by dipping the porous layer of the body in a solution of platinum salt in a volatile solvent, such as acetone, and allowing the solution to wick into the porous layer. The preferred platinum "salt" is hexachloroplatinic acid, and the term "salt" as used throughout the specification and claims will be understood to include acids. The solvent preferably wets the ceramic. The body is then fired to drive off the solvent and reduce the platinum salt to a 0.01 to 0.5 micron layer of platinum, with numerous unplated areas. The activated body is then plated by electroless plating procedures to grow a coating of about one to ten microns of platinum on the first surface. The coating is permeable to oxygen at the intersections of crystals emanating from individual activation sites. The platinum coating is mechanically locked into the spherical recesses during the plating process.

In accordance with another aspect of the invention, a method is provided of forming a solid electrolyte cell, the method comprising a step of forming a body including an elongate body formed of a solid electrolyte compact, thereafter a step of drilling an axial cavity in the body, and thereafter a step of firing the body to densify it. Preferably the body is formed by uniaxially compressing a zirconia powder into a thimble having a tapered bore, and then drilling out the tapered bore to form a substantially cylindrical cavity.

In accordance with another aspect of the invention, an oxygen sensor is provided including a thimble-shaped electrolytic cell having an interior defined by a substantially cylindrical wall, an electrical contact on the wall, an elongate electrical terminal extending from outside the cell into the interior of the cell, the terminal including a pair of arms, at least one of the arms engaging the contact on the wall, and an elongate electrical heater extending into the interior of the cell, the terminal arms embracing the heater and positioning the heater in the cell.

DESCRIPTION OF THE PREFERRED EMBODIMENT

Figure 1:
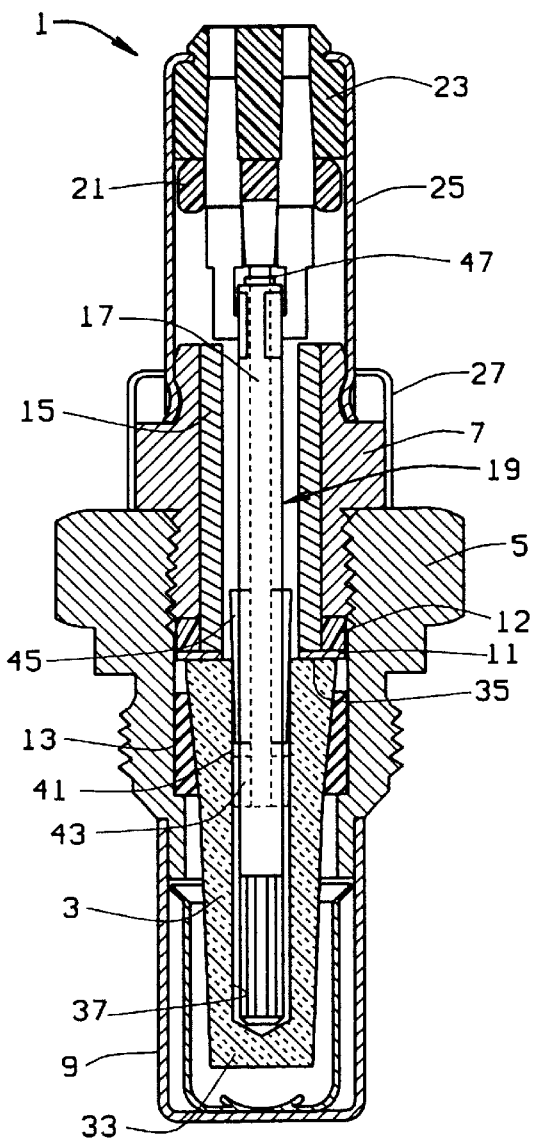
FIG. 1 is a cross-sectional view of a preferred oxygen sensor of the present invention.
Figure 2:
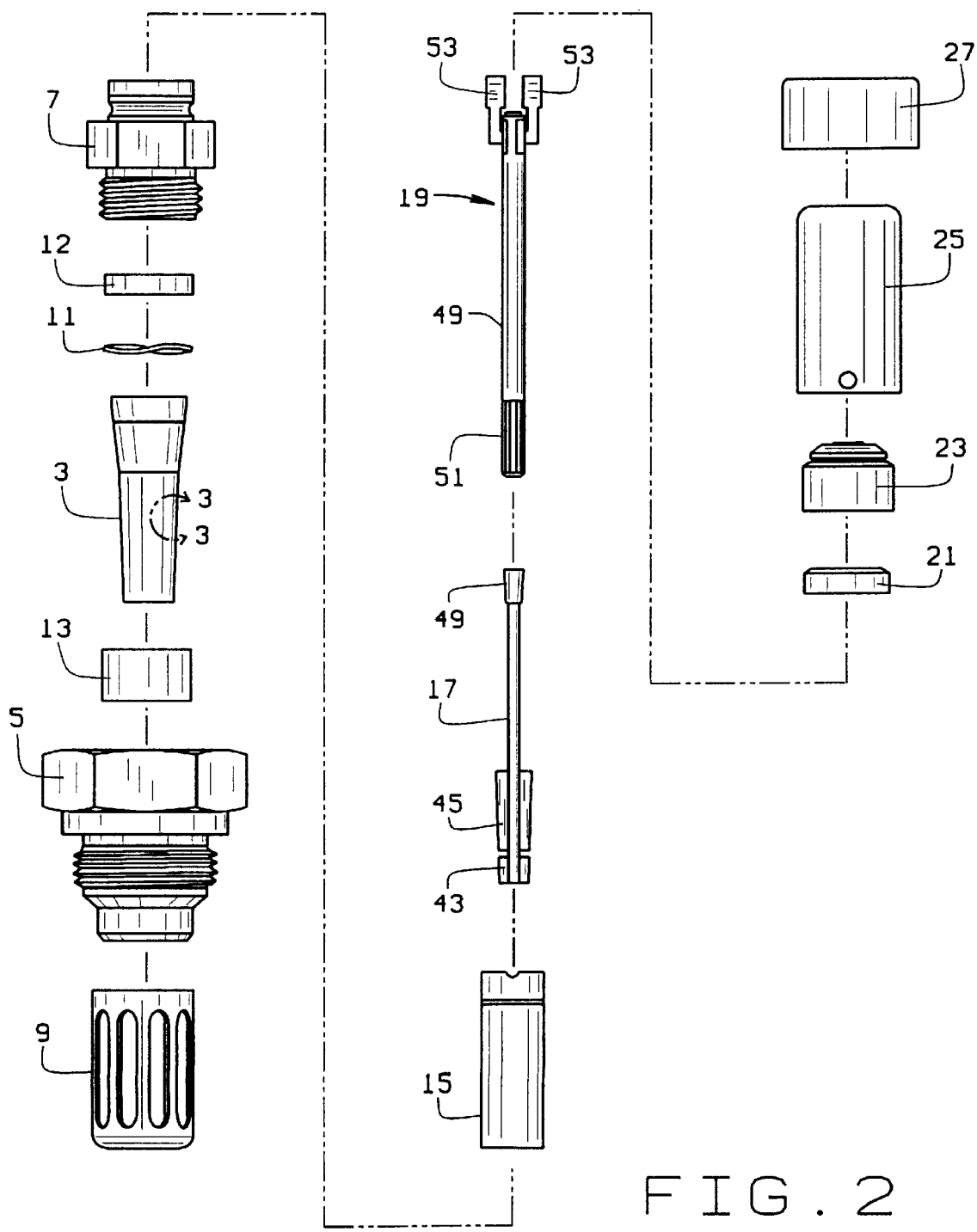
FIG. 2 is an exploded view of the sensor of FIG. 1.

Referring now to the drawings, and in particular to FIGS. 1 and 2, reference numeral 1 indicates a preferred embodiment of automotive exhaust gas lambda oxygen sensor of this invention. The sensor 1 is in most respects similar in construction to that shown in FIGS. 1–8 of Wolfe, et al., U.S. Pat. No. 5,049,255, and to the construction of an oxygen sensor commercially available from Tomco, Inc., of St. Louis, Mo. The overall construction and operation of the sensor 1 are well known to those skilled in the art.

In brief, the oxygen sensor 1 includes a cell 3, a lower body 5, an upper body 7, a shroud 9, a wave washer 11, a spacer 12, a graphite seal 13, an insulator 15, a terminal 17, a heater assembly 19, a button 21, a grommet 23, a debris shield 25, and a tamper-proof shield 27.

The cell 3 includes a body 31 formed as a thimble, i.e., as a hollow conical frustum having a closed lower end 33 defined by a wall and an open upper end 35. The body 31 is about 2.5 cm tall, 1.0 cm in diameter at its upper end and 0.6 cm in diameter at its lower end. The body flairs slightly at its upper end. A central axial bore 37 has a diameter of 0.3 cm and a depth of about 2.3 cm. The body 31 is formed of 5% yttria stabilized zirconia. On the exterior of the body 31 is a uniform coating 39 of platinum, the coating having a thickness of about one to twenty microns, preferably about one to ten microns. The coating 39 extends to about 0.4 cm from the top edge of the body. The wall of the bore 37 includes a platinum stripe 41 extending from the bottom of the interior bore 37 to the top of the bore, the stripe having a thickness of about ten to sixty microns.

The lower body 5 is internally tapped and threaded to form a bore which receives the seal 13, cell 3, wave washer 11 and spacer 12, all of which are held snugly in place by the externally threaded upper body 7. The graphite seal 13 is pressed against the lower body 5 and forms an electrical connection between the outer face of the cell 3 and the body. The shroud 9 is welded to a lower end of the lower body part 5 and protects the lower end of the cell 3.

The upper body 7 includes an axial bore, of smaller diameter than the bore of the lower body 5, which receives the insulator 15. The insulator 15 is a ceramic sleeve which electrically isolates the terminal 17 from the body 5 and 7.

The terminal 17 extends through the insulator 15, spacer 12, and wave washer 11, into the bore 37 of the cell 3. Two lower arms 43 and two upper arms 45 are provided at the lower end of the terminal 17. The upper terminal arms 45 are proportioned to form a good electrical contact with the platinum stripe 41 on the inside of the body 3 and to hold the terminal 17 frictionally in the cell 3. The lower arms 43 are proportioned to receive the heater assembly 19, rather than an electric wire as in Wolfe, et al., U.S. Pat. No. 5,049,255. Electrical connection is made to the terminal 17 by welding or crimping a lead wire (not shown) to a head part 47.

The heater assembly includes an elongate sheath 49 having a resistance heater 51 at its lower end with leads running through the sheath to terminals 53 at the upper end of the heater. The terminals 53 have welded or crimped to them electrical wires (not shown). The heater 51 extends to near the bottom of the bore 37 of the cell 3. The lower terminal arms 43 surround, support, and guide the sheath 49 of the heater assembly 19 to maintain its axial position in the bore 37 of the cell 3. Although the oxygen sensor 1 will operate without the heater assembly 19, the cell will be brought to operating temperature far more quickly by operating the heater 51 when the automobile engine is started, as is well known in the art. The design of the heater assembly 19 and uniform cylindrical bore 37, provide rapid and uniform heating of the cell 3, to provide rapid warm-up times for the cell, thereby decreasing pollutants more quickly when the engine is started.

The upper end of the upper body 7 is closed by the button 21 and the grommet 23, which is held by the turned upper edge of the debris shield 25. The debris shield is friction-fitted to the upper end of the upper body 7, and the tamper-proof shield 27 is friction fitted over it and a hex-nut portion of the upper body 7 to discourage disassembly of the body. The button and grommet have bores in them aligned with the terminals 53, to permit passage of the wires welded to the head 47 and terminals 53.

The constructions of the parts other than the cell 3 are well known to or easily determined by those skilled in the art.

The cell 3 is constructed as follows.

A 5% yttria zirconia powder in an acrylic binder is lubricated with a fatty acid such as palmitic acid in an ethanol vehicle. The powder has an average particle size of less than one micron. The powder is dried in air and uniaxially pressed at a pressure of 2,000 to 15,000 pounds, preferably 3,000 to 4,000 pounds, into a thimble compact having a mirror outer surface. A tapered mandrel forms a central tapered bore in the compact. The compact is bored with a diamond drill to form a uniform cylindrical bore having a central point at its lower end remaining from the bore formed by the mandrel. Drilling the bore, rather than machining the exterior of the thimble compact as is generally done, reduces the labor required. The compact is then dipped in an alcohol slurry of stabilized zirconia powder and spray-dried stabilized zirconia granules to deposit a coating about fifty microns thick. A preferred composition of the slurry is:

| | |
|---|---|
| 4.5 mole percent yttria-stabilized zirconia with acrylic binder (spray dry granules - 200–250 mesh) | 48.00 g. |
| 3.0 mole percent yttria-stabilized zirconia (powder - <1μ particles) | 24.83 g. |
| $Y_2O_3$ (1–5μ particles) | 0.77 g. |
| $Al_2O_3$ (1–10μ particles) | 6.40 g. |
| EtOH (denatured absolute) | 187 ml. |
| Fish oil | 2.67 g. |
| Polyvinyl butanol (PVB) | 0.85 g. |

The ethanol and fish oil are shaken until dissolved. The stabilized zirconium oxide powder, yttria, and alumina are added and rolled overnight. PVB is added and rolled thirty to forty-five minutes, then most of the beads are removed. The spray-dried granules are added and rolled five minutes. The mixture is agitated to maintain the granules in suspension.

The coated compact is dried in ambient air and then fired to a temperature of 1440° C. and held for two hours in air. Firing is accomplished in stages; first raising the temperature to 350° C. over seven hours, holding for one hour, then raising to 550° C. over seven hours and holding three hours, before raising to 1440° C. for two hours. The part is cooled rapidly, at a rate of 5° C. per minute. The firing process burns off the acrylic binder and reduces the dimensions of the thimble by about twenty-five percent. The resulting thimble has a body which is smooth, dense and nonporous, covered with an external coating 55 which is highly porous. The coating is chemically bonded to the body. If the body were formed entirely of the coating, it would be worthless as a solid electrolyte for an oxygen sensor, because it would conduct air. In the firing process, the spray-dried granules in the coating shrink away from the matrix forming the coating and form spherical voids 57 in the matrix, with the densified granules bonded to their interiors. These spherical voids play an important part in the plating process as described hereinafter. The porous coating also includes many smaller voids which likewise play an important role in the plating process.

After the compact has been fired and densified to form the body, interior and exterior electrodes are applied.

The interior electrode 41 is painted on as a stripe of platinum ink, to form a thick film electrode. The thimble body is again fired in air to a temperature of 1280° C. and held for two hours.

The thimble body is cooled, then dipped in an activation bath containing about fifty grams of platinum as hexachloroplatinic acid (122.3 g hexachloroplatinic acid hexahydrate) per liter of acetone. The solution is wicked up into the porous coating 55, and the platinum deposits on discrete sites on the surface. The solution preferably does not wick onto the upper 0.3 cm of the thimble body. The activated thimble is then dried and fired in air to 700° C. for two hours. The activation process produces a large number of nucleation sites having a coating of pure platinum with a thickness of about 0.01 to 0.5 microns, preferably 0.1 to 0.5 microns.

The activated thimble is immersed in boiling water for two minutes, then immersed in cold dilute hydrochloric acid (pH 2 to 5), then immersed in an electroless plating solution which is raised in temperature from room temperature to 80° C. and held for approximately forty minutes. The plating solution preferably has the following composition:

| | |
|---|---|
| Distilled water | 375 ml. |
| Concentrated HCl (30%) | 32 ml |
| Ethanol (denatured 200 proof) | 2.75 ml |
| Chloroplatinic acid (0.1 g./ml. Pt) | 23.0 ml |
| Hydrazine dihydrochloride (0.200 g./ml.) | 11.5 ml |

Dilute with distilled water to 458 ml.

The foregoing solution will plate eighty-eight thimbles simultaneously to a thickness of about three microns, while depleting the plating bath. Coatings from about one to about fifteen microns are believed to produce acceptable sensors, although the acceptable thicknesses are determined empirically. In theory, any coating which is conductive (provides electrical continuity) and which permits oxygen to permeate the solid electrolyte body should be operable. Because nearly all of the platinum in the plating solution is applied to the parts, and the remainder is easily recovered, the process is extremely efficient and cost-effective.

The temperature of the plating solution is also determined experimentally for a particular purity and source of chloroplatinic acid, the temperature being chosen to provide complete plating without precipitation of the platinum.

Figure 3:
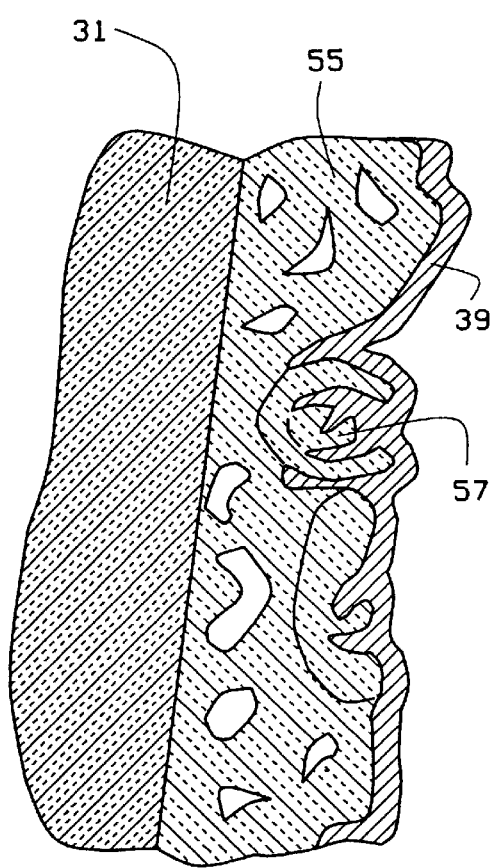
FIG. 3 is a cross sectional view of a photomicrograph of a surface of an electrolytic cell of the oxygen sensor of FIGS. 1 and 2, plated in accordance with the present invention.

The electroless plating process provides coatings of great uniformity. As shown in FIG. 3, unlike the results of painting a thick film ink onto the surface or sputtering a film onto the surface, the plated film extends into the pores of the porous coating, including the spherical openings produced by the densified granules in the coating. The platinum film is thus locked into the pores and cannot be peeled from the surface of the thimble. Because the film is grown from a large number of nucleation sites, numerous intersecting crystals are formed, which provide numerous domain boundaries. The film is of uniform thickness from the bottom of the cell to the top of the coating, unlike a sputtered coating which is much thicker at one end.

After the plating step is completed, the cell 3 is rinsed repeatedly in distilled water and fired in air to 700° C. to burn off any impurities. The cell is then flame sprayed to give it a protective spinel coating, as is conventional in the art.

The completed cell 3 is assembled into a sensor as shown in FIG. 2. The sensor was tested in a 1988 Oldsmobile against other commercially available oxygen sensors and was found to have operating characteristics better than all but the best. It has switching times of about 160 milliseconds and prompt, accurate switches from 600 millivolts to 300 millivolts in a snap throttle test. Even without the heater, it reaches operating temperatures moderately quickly and operates well at lower temperatures, such as idle temperatures. The thin wall and aspect ratio (length-to-diameter) of the cell 3 provide rapid heating of the cell both by the heater 19 and by ambient exhaust gasses. It is believed that still better results may be obtained with different thicknesses of the exterior electrode 39 and by applying a more uniform inner electrode.

Numerous variations in the cell, method and sensor of the present invention, within the scope of the appended claims, will occur to those skilled in the art in light of the foregoing disclosure. For example, the body of the cell may include up to twenty percent alumina. The alumina makes the cell physically stronger, draws silica impurities (so that the grain boundaries are zirconia to zirconia), helps increase thermal conductivity, and reduces cost.

The cell, or a modification of it, can be used with non-stoichiometric (e.g., pumping type) oxygen sensors of totally different geometries.

It has been found that the sensor 1 is an efficient oxygen generator when connected to a current source. Likewise, the cell may be used as a current generator when connected in an exhaust stream of a combustion process.

The plating technique may be used with other electrodes and to plate a precious metal on other substrates which have a porous surface. The porous surface can be a porous coating or, in accordance with broader aspects of the invention, may be a part of the substrate itself. The precious metal may include gold, silver, the platinum metals (platinum, rhodium, palladium, osmium, ruthenium, and iridium), or mixtures thereof. The activation step may include forming nucleation sites of other metals, for example tin and palladium. These examples are merely illustrative.

We claim:

1. A method of forming a solid electrolyte cell comprising forming a solid electrolyte body as a thimble with an outer surface and an inner surface, forming a porous layer on the outer surface of the body, activating the porous layer on the outer surface of the body to form a plurality of growth points for a conductive layer on the outer surface, growing a first electrode by electroless plating of a conductive layer on the activated porous layer on the outer surface of the body, and forming a second electrode on the inner surface of the body, the method further comprising drilling axial cavity in the thimble, and thereafter firing the body to densify it.

2. The method of claim 1 wherein the step of forming a solid electrolyte body comprises forming a body which is impervious to air.

3. The method of claim 1 wherein activating the porous layer on the outer surface comprises wicking a metal salt carried by a liquid into the porous layer.

4. The method of claim 1 wherein growing a first electrode comprises immersion of the porous layer on the outer surface in an unstable solution of a salt of a metal.

5. The method of claim 1 wherein the body is formed by uniaxially compressing a zirconia powder into a thimble having a tapered bore, and then drilling out the tapered bore to form a substantially cylindrical cavity.

6. The method of claim 1 further comprising inserting into the thimble an elongate electrical terminal extending from outside the cell into the interior of the thimble, the terminal including a pair of arms, at least one of the arms engaging the second electrode.

7. The method of claim 6 further comprising inserting into the thimble an elongate electrical heater extending into the interior of the thimble, the terminal arms embracing the heater and positioning the heater in the thimble.

8. The method of claim 3 wherein the liquid is an organic solvent which wets the ceramic.

9. The method of claim 8 wherein the organic solvent is acetone.

10. The method of claim 3 including a step, after wicking the solution into the pores at the surface of the substrate, of heating the substrate to drive off the liquid and reduce the salt to a 0.01 to 0.5 micron layer of a metal with numerous unplated areas.

* * * * *